(12) United States Patent
Gudmundsson

(10) Patent No.: US 9,448,142 B2
(45) Date of Patent: Sep. 20, 2016

(54) MILK SAMPLING

(75) Inventor: Mats Gudmundsson, Sodertalje (SE)

(73) Assignee: DELAVAL HOLDING AB, Tumba (SE)

( * ) Notice: Subject to any disclaimer, the term of this patent is extended or adjusted under 35 U.S.C. 154(b) by 364 days.

(21) Appl. No.: 13/991,449

(22) PCT Filed: Dec. 20, 2011

(86) PCT No.: PCT/SE2011/051546
§ 371 (c)(1),
(2), (4) Date: Jun. 4, 2013

(87) PCT Pub. No.: WO2012/087235
PCT Pub. Date: Jun. 28, 2012

(65) Prior Publication Data
US 2013/0247692 A1 Sep. 26, 2013

Related U.S. Application Data

(60) Provisional application No. 61/426,120, filed on Dec. 22, 2010.

(30) Foreign Application Priority Data

Dec. 21, 2010 (GB) .................................. 1021826.1

(51) Int. Cl.
G01N 1/20 (2006.01)
G01N 1/10 (2006.01)
A01J 5/04 (2006.01)

(52) U.S. Cl.
CPC ........... G01N 1/10 (2013.01); A01J 5/045 (2013.01)

(58) Field of Classification Search
CPC ............. A01J 5/01; A01J 5/045; G01F 1/00;
G01F 3/38; G01F 5/00; G01N 35/1097;
G01N 1/14; G01N 1/2252; G01N 1/10;
Y10T 436/2575; Y10T 436/25
USPC ...................................... 73/863.002
See application file for complete search history.

(56) References Cited

U.S. PATENT DOCUMENTS 4,900,683 A * 2/1990 Metzger ............... G01N 1/28
436/174
5,441,071 A * 8/1995 Doherty ............... G01N 1/18
137/15.05

(Continued)

FOREIGN PATENT DOCUMENTS

CN 1250164 A 4/2000
CN 1452716 A 10/2003

(Continued)

OTHER PUBLICATIONS

"Milk Quality Control—Somatic Cell Count Indicator", Operator Manual, Lely Industries N. V. Dairy Equipment, Initial Issue Jun. 2007, D-H004.0706EN.

(Continued)

Primary Examiner — Eric S McCall
Assistant Examiner — Mohammed E Keramet-Amircola
(74) Attorney, Agent, or Firm — Young & Thompson

(57) ABSTRACT

A milk sampling system for use with an automatic milking machine includes a metering pump (2) having an inlet (9) connected to a induction system (3) and an outlet (10) connected to a discharge system (5). The induction system includes a manifold block (4) with passages forming supply paths (12, 13, 15) for connecting the pump inlet to a milk source, a washing fluid source, and a source of pressurized air, and solenoid valves (21, 22, 25) to selectively open and close the supply paths. The discharge systems includes a manifold block (6) with passages forming a plurality discharge paths (27, 29, 31, 33) for successively delivering discrete milk samples for analysis, and solenoid valves (35, 36, 37, 38) to selectively open and close the discharge paths.

20 Claims, 5 Drawing Sheets

(56) References Cited

U.S. PATENT DOCUMENTS

| | | | |
|---|---|---|---|
| 6,332,349 | B1 | 12/2001 | Poynot |
| 6,814,028 | B2* | 11/2004 | Watanabe .................. A01J 5/00 119/14.44 |
| 7,611,842 | B2 | 11/2009 | Deppermann et al. |
| 2002/0124803 | A1* | 9/2002 | Chen .......................... A01J 5/01 119/14.08 |
| 2003/0143748 | A1* | 7/2003 | Gudmundsson ........ A01J 5/045 119/14.02 |
| 2004/0028565 | A1 | 2/2004 | Abou-Saleh et al. |
| 2004/0194712 | A1* | 10/2004 | Johannesson ......... A01J 5/0134 119/14.18 |
| 2005/0223996 | A1* | 10/2005 | Bosma ....................... A01J 5/01 119/14.02 |
| 2006/0283269 | A1* | 12/2006 | Anderson ................. A01J 5/04 73/863.31 |
| 2009/0007847 | A1* | 1/2009 | Relin ..................... A01J 5/0075 119/14.02 |
| 2009/0199769 | A1* | 8/2009 | Tucker .................... A01J 5/017 119/14.02 |

FOREIGN PATENT DOCUMENTS

| | | | |
|---|---|---|---|
| CN | 1471639 | A | 1/2004 |
| CN | 101526541 | A | 9/2009 |
| EP | 0709666 | | 5/1996 |
| EP | 1381269 | | 10/2004 |
| EP | 1267609 | | 1/2005 |
| NZ | 525317 | A | 3/2006 |
| RU | 2007110842 | | 10/2008 |
| SU | 1428318 | | 10/1988 |
| SU | 1731106 | | 5/1992 |
| WO | 02069697 | A1 | 9/2002 |
| WO | 03/090522 | | 11/2003 |
| WO | 2004/057305 | | 7/2004 |
| WO | 2004111613 | A2 | 12/2004 |
| WO | 2005093387 | A1 | 10/2005 |

OTHER PUBLICATIONS

Lely Astronaut, "Robotic Milking system", publication of Lely Group.
"Lely Astronaut A4.wmv", video available online at https://www.youtube.com/watch?v=8ONf6DxTnos, uploaded on Nov. 16, 2010.
"Lely Astronaut A3 Milking Robot", video available online at https://www.youtube.com/watch?v=1Vo4NJU5wTk, uploaded on Aug. 16, 2007.
"Lely Astronaut A3 SouthlandNZ.wmv", video available online at https://www.youtube.com/watch?v=IY1bF__5bUBg, uploaded on Dec. 7, 2008.
Notice of Opposition to Grant of Patent filed in a corresponding application.
International Search Report dated May 8, 2012, corresponding to PCT/SE2011/051546.
British Search Report dated Apr. 21, 2011, corresponding to the Foreign Priority Application No. GB1021826.1.
Supplemental International Search Report dated Mar. 28, 2013, corresponding to PCT/SE2011/051546.
Chinese Office Action, dated Jun. 16, 2014, from corresponding CN application.
Third Party Observation, dated Jul. 1, 2014, from corresponding EP application,.

* cited by examiner

MILK SAMPLING

BACKGROUND OF THE INVENTION

1. Field of the Invention

This invention is concerned with milk sampling. The invention is more especially although not exclusively concerned with sampling milk in connection with the milking of animals, such as by an automated milking apparatus capable of milking animals without human supervision. There are known, for example, installations in which animals are free to visit a milking machine when they choose, and the milking machine is adapted to identify an animal visiting the machine and to decide if that animal is due to be milked. The automatic milking machine includes a robot arm for attaching teat cups to the teats of the animal if it is to be milked and a vacuum system to perform the actual milking. The milk extracted from the udder of the animal is conducted to a receiving vessel and, unless it is deemed of unacceptable quality for collection in which case it may be diverted and either discarded or collected for other use, the milk is subsequently delivered from the receiving vessel to a bulk storage tank in which the milk from an entire herd of animals may be accumulated and stored, the tank then being emptied once a day or every few days. For checking milk quality and for collecting data which can be helpful for herd management and for monitoring animal condition and state of health, it is usual for milk samples to be taken at the time of milking individual animals and subsequently analysed. Traditionally the samples from the respective animals are collected in small containers, such as sample tubes or the like, and the sample tubes with their contents are taken to a remote laboratory where an analysis of the milk samples is carried out. Sampling in this manner is generally performed regularly but only periodically such as once a month. In recent times analysers capable of analysing milk at or near to where the animals are milked have been developed and analysing equipment of this kind can have the advantage of the analysis results reaching the farm manager much quicker so that appropriate actions may be taken sooner to aid efficient milk production and the best possible animal welfare.

2. Description of the Related Art

In EP 1381269B there is described milk sampling and analysis of the latter kind. The milk analysing apparatus is arranged to analyse separately respective portions of a milk sample in order to provide, on a real time basis, quantitative measurements on a combination of compounds and parameters present in the milk samples from individual herd members or a group of herd members so as to derive from the samples data relating to the health condition, the physiological condition, the nutritional and energy state, the state of the oestrus cycle and pregnancy. Thus, the analysis can aid optimal utilisation of feed rations by implementation of feeding schemes on an individual animal or group basis, tight control of subclinical and clinical disease conditions that affect milk production and composition, optimal reproduction control and reliable pregnancy detection. Not every analysis is performed on every milk sample and a means is included for directing the milk sample portions to the separate analysing means only as desired, such as at pre-selected points of time, or pre-selected time intervals in the reproduction and/or lactation cycles. For obtaining the milk samples for analysis EP 1381269131 proposes automatic on-line collection at the milking site from the milking system and automatic transfer to the analytical means. The milking site may be the milking site of an automatic milking system for freely moving animals, or one of several milking sites in a more conventional milking system such as a herringbone milking system, or a rotating carousel type of milking parlour, or a parallel milking parlour. More specifically, for collecting milk samples from individual animals there is suggested in EP 1381269B1 a collecting means for collecting a proportional milk sample which is representative of the average composition of the total milk produced during the milking of each animal, and comprising a container for storing the sample, which container may be pressurised above the pressure of the milking system for subsequent and/or parallel transport of subsamples to the analysing means. Additionally the sample collecting means can comprise means for apportioning a milk sample to the analysing means, whereby a total sample is divided into one or more subsamples which is/are transported to the analysing means while a remaining part of the sample may be led to the bulk milk tank or discharged. While the milk collecting means is generally described in these terms in EP 1381269, no specific sample collecting arrangement adapted for use with an automatic milking machine is disclosed.

In EP 1267609 B1 there is described a milk sampling arrangement for use with an automated milking system and adapted to deliver milk samples to storage tubes for subsequent transport to a remote laboratory for analysis. The sampling arrangement includes a milk collection vessel into which a representative amount of milk, e.g. about 2% of the total amount of milk from an animal milking, is delivered from a conduit or vessel of the automated milking system. The collection vessel has two different discharge outlets at different heights, the upper outlet being connected to a discharge line and the lower outlet being at the bottom of the vessel and connected to one end of a hose having a filling member at the other end. The filling member is positionable over a selected sample tube by an X-Y positioning system. After all the milk to be collected from an animal milking has flowed into the vessel, compressed air is supplied to the vessel to stir the milk. The major part of the milk in the vessel is then discharged through the upper discharge outlet and may be thrown away, returned to the automated milking system or transported to the milk tank. A certain quantity of milk then remains in the lower part of the vessel and this milk sample is delivered through the lower discharge outlet to pass to the filling member and to the selected collection tube. The arrangement is suitable for collection of single milk samples in respective collection tubes.

BRIEF SUMMARY OF THE INVENTION

The object of the present invention is to provide a simple and convenient system for collection of milk and delivery of a plurality of milk samples, such as collection of milk from an automotive milking machine, and delivery of one or more samples directly to milk analysing means, for example of the kind described in EP 1381269 B1.

In accordance with a first aspect the present invention provides a milk sampling system comprising a fluid conveying device arranged to receive milk from a milking machine and a control device configured to control the fluid conveying device to forward discrete samples of the milk to respective discharge paths for analysis, the fluid conveying device comprising a pump having an inlet connected to an induction system and an outlet connected to a discharge system, the induction system having supply paths arranged to selectively connect the pump inlet to a plurality of fluid sources including a milk source, and the discharge system having a plurality of discharge paths arranged to successively deliver discrete milk samples to the respective discharge paths for analysis.

The milk sampling system of the invention enables the preparation and delivery of discrete milk samples of predetermined quantity in a simple and convenient way. Sophisticated control arrangements are not needed. Thus, the need for sensors can be avoided, and the control device can control operation of the fluid conveying device by simple control of the pump and to open and close valves in an appropriate sequence, as will become apparent from the detailed description which follows.

In a preferred embodiment of the milk sampling the pump is a metering pump, such as a membrane pump which may be calibrated to deliver a fixed quantity, e.g. 2 ml, for each stroke of the pump.

The induction system can comprise a manifold block carrying devices for selectively opening and closing the supply paths, at least one and preferably each of these devices being a valve, such as a solenoid valve. Similarly the discharge system may comprise a manifold block carrying devices for selectively opening and closing the discharge paths, at least one and preferably each of these devices being a valve such as a solenoid valve. The solenoid valves can be membrane valves which generally have a low power requirement, and the valves may have a normal off condition so that the valves are closed when the actuators are not energised.

The induction and discharge manifold blocks form respective modules or units which are conveniently mounted together with a pump unit disposed therebetween to provide a simple and compact assembly.

The milk source is conveniently a chamber for receiving a representative milk sample from the milking of an individual animal by an automatic milking machine, the chamber having an inlet for the milk to enter the chamber and an outlet at the bottom that is connected to a milk supply path in the induction system, which along with the other supply paths can be defined by a duct or passage in the induction manifold block. The chamber may have a closeable connection to atmosphere for venting displaced air from the chamber as it is filled with milk.

The induction system may include a drain path and a device, such as solenoid actuated membrane valve, for selectively opening and closing the drain path. If desired the drain path can also be opened to admit air into the milk collection chamber via the milk supply path and the milk outlet of the chamber, the air being drawn into the chamber by vacuum supplied from the automatic milking machine and bubbling through the milk in the chamber to agitate and mix the milk.

The plurality of fluid sources connectable to the pump inlet through supply paths in the induction system may include a source of washing fluid, in which case the induction system may be equipped with a washing fluid pressure control device in the supply path for the washing fluid. The plurality of fluid sources may include alternatively or additionally a source of pressurised gas in particular air, and the induction system can include a pressure control device in the supply path for the pressurised gas, or a plurality of control devices for pressurised gas to be supplied at different pressures. The pressurised gas can also be used to push a milk sample discharged through a sample discharge path to an analysing means. The pressurised gas can also be used for drying the sample discharge paths and lines after they have been cleaned with washing fluid.

The milk sampling system preferably includes a control devices which operates so that after delivery of a milk sample through at least one discharge path, washing fluid is supplied through the washing fluid supply path and is conveyed through the pump and through the at least one discharge path, and subsequently drying air is supplied through the pressurised gas supply path and is conducted through the pump and through the at least one discharge path. By passing washing fluid through a milk sample discharge path after a sample has been discharged through that discharge path, the washing fluid will flush away any remnants of the milk sample from the discharge path before the next sample is discharged through this path. Passing a drying gas, such as air, through the discharge path after the washing fluid effectively removes any washing fluid. In this way one milk sample is prevented from contaminating a following milk sample and the milk samples will not be contaminated or diluted by the washing fluid either.

The induction system can comprise a milk return path for returning milk to the automatic milking machine for it to be collected in the milk tank with other milk, and a device for selectively opening and closing the milk return path. In this way milk waste can be minimised.

The discharge system may include a drain path through which milk or other liquid can be discharged to drain, and a device, such as a solenoid actuated membrane valve, for opening and closing the drain path.

BRIEF DESCRIPTION OF THE DRAWINGS

The foregoing and other features and advantages of the invention will become apparent and better understood from the following detailed description which is given by way of example only and with reference to the accompanying drawings in which.

DETAILED DESCRIPTION OF THE PREFERRED EMBODIMENTS

Figure 1:
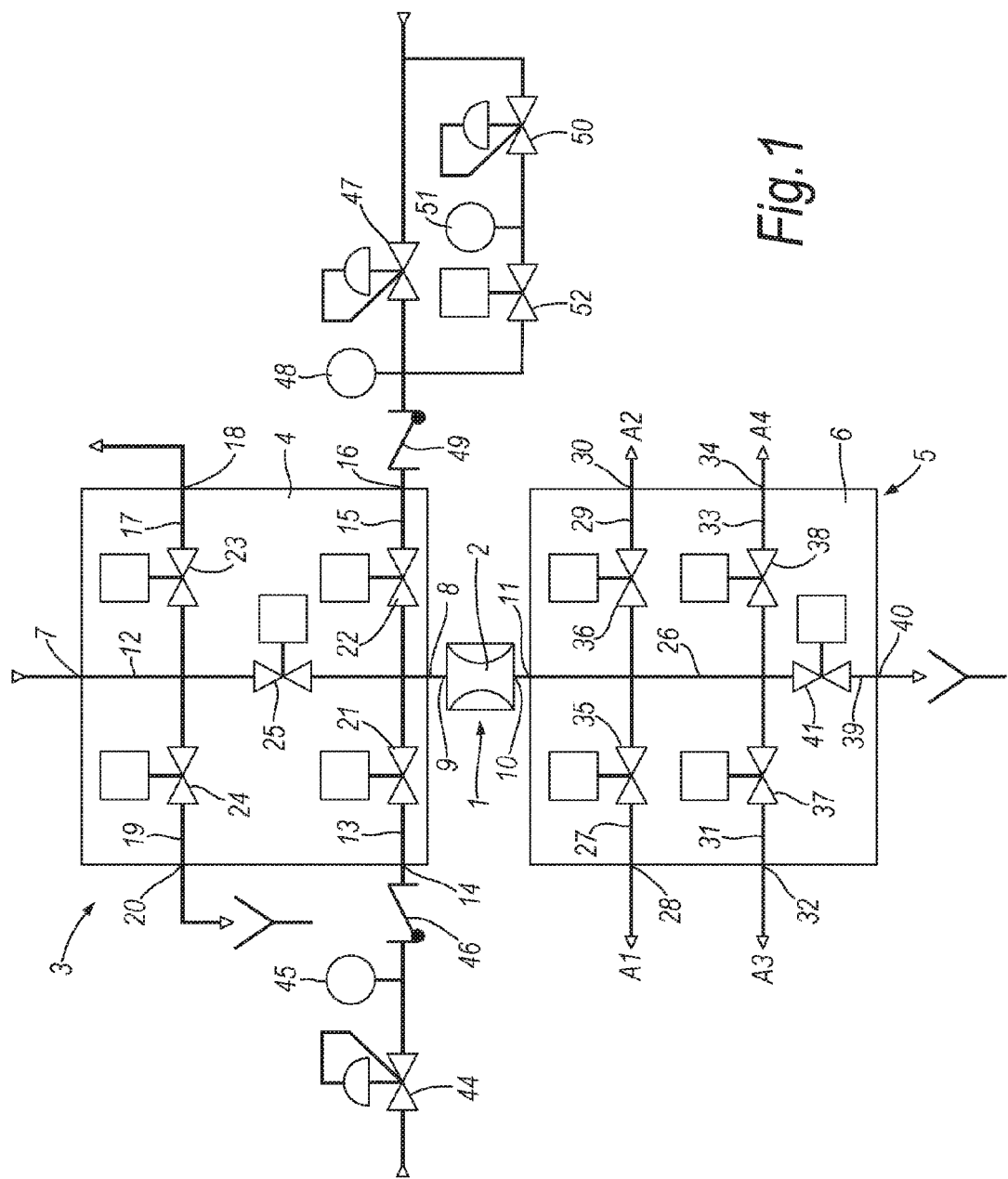
FIG. 1 is a schematic representation of a milk sampling system in accordance with present invention.
Figure 2:
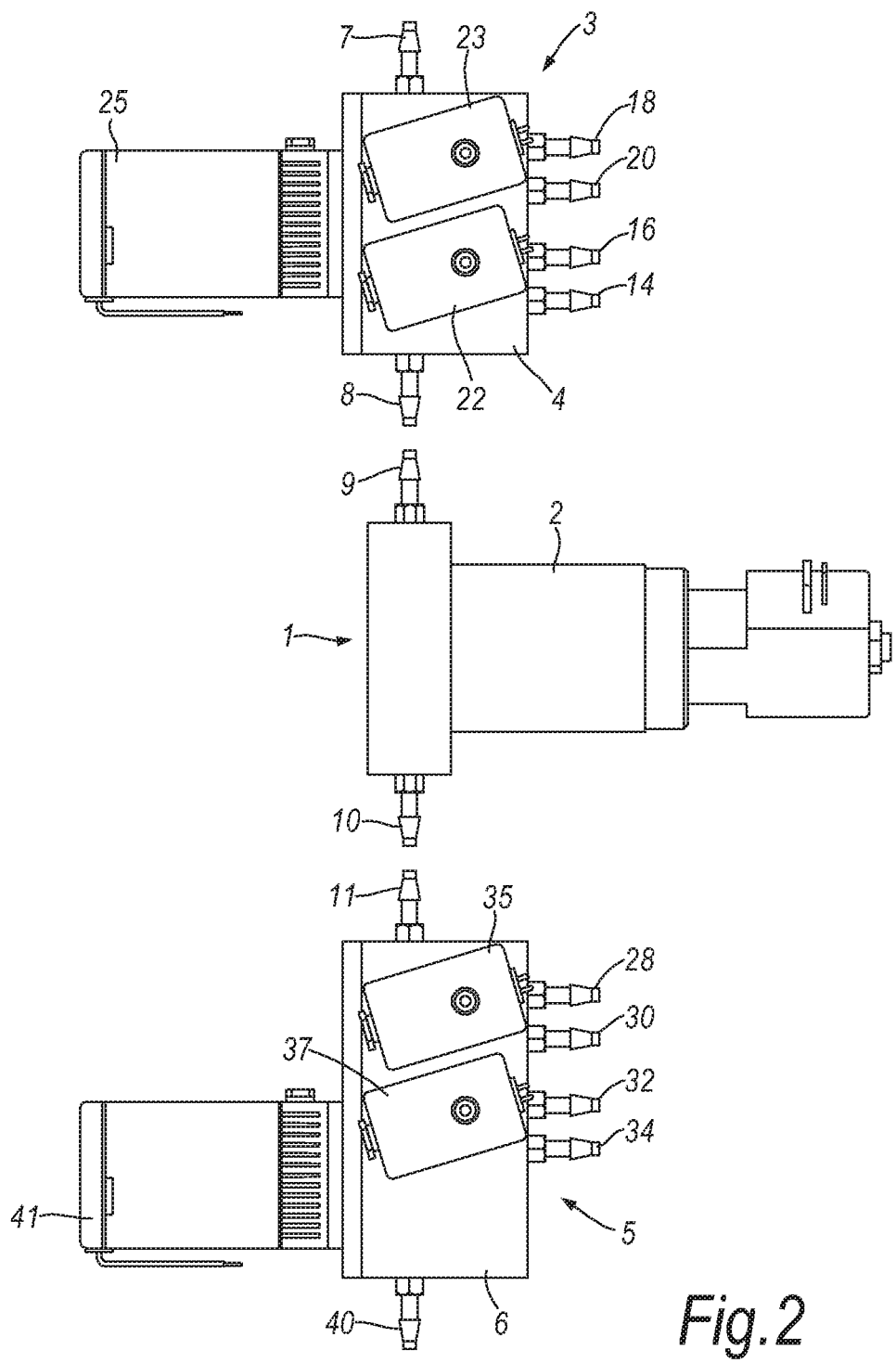
FIG. 2 is a front elevation of a pump unit and valve module assembly of an apparatus as shown in FIG. 1.
Figure 3:
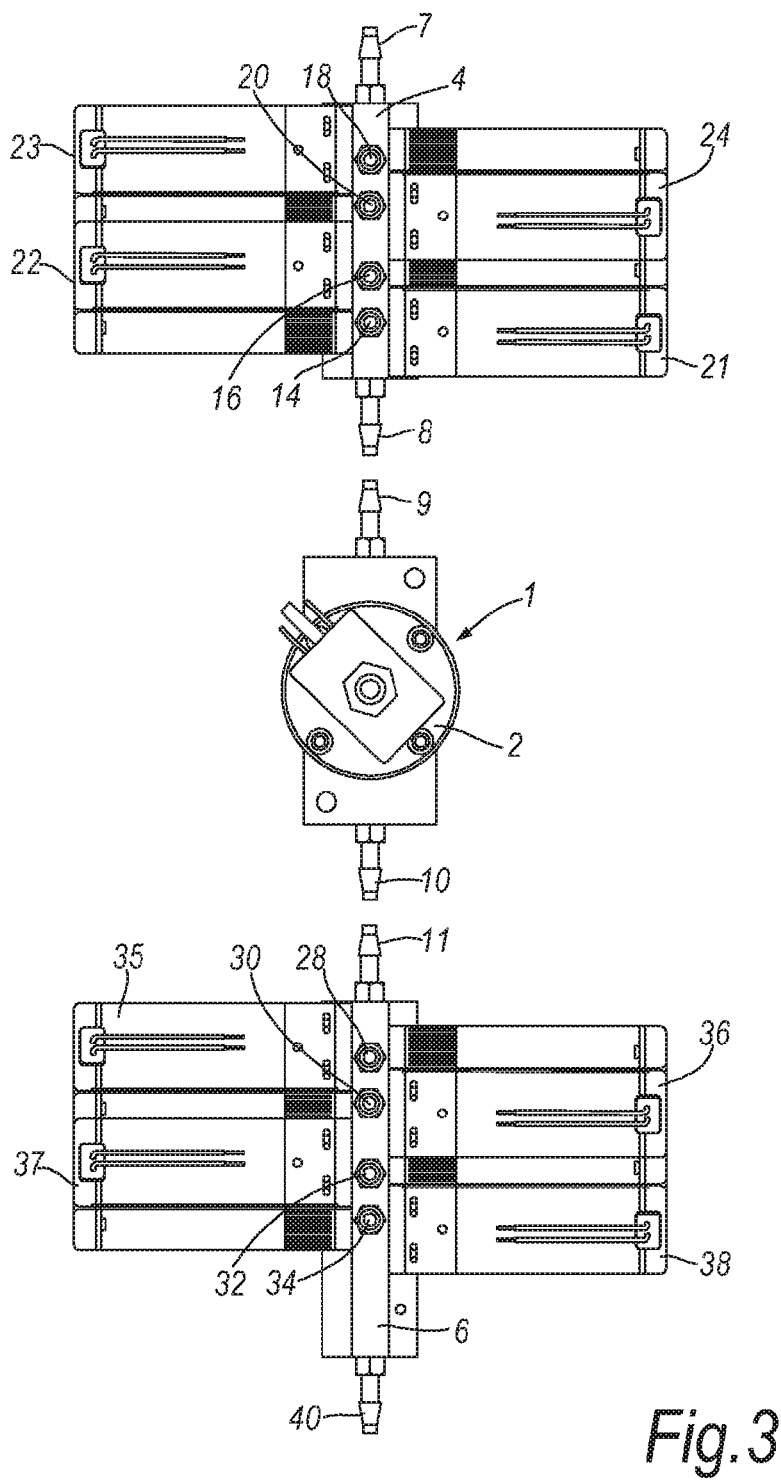
FIG. 3 is a side elevation of the assembly shown in FIG. 2.
Figure 4:
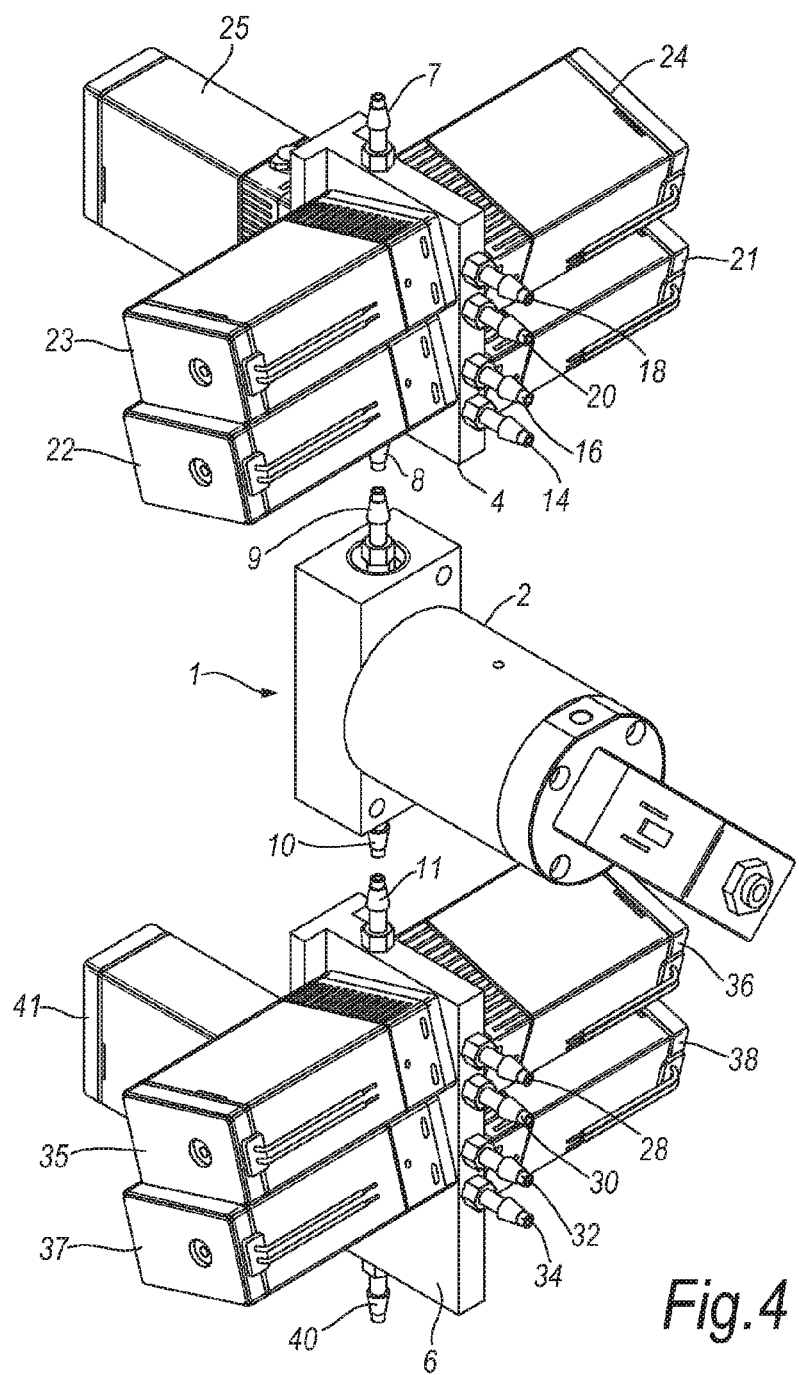
FIG. 4 is a isometric view of the assembly shown in FIGS. 2 and 3.

A milk sampling system embodying the invention is illustrated in FIGS. 1 to 4, and as shown it comprises a fluid conveying device with a pump unit 1 including metering pump 2, in particular a membrane pump calibrated to discharge a fixed quantity of liquid for each stroke of the pump, an induction system 3 including a manifold block 4, and a discharge system 5 including a manifold block 6. The manifold block 4 includes an inlet nipple 7 for connection to a milk source, to be described in more detail below, by a connecting tube, and an outlet nipple 8 for connection to an inlet nipple 9 of the pump unit 1 by a short connecting tube, not shown in FIGS. 2-4. The pump unit 1 has an outlet nipple 10 for connection to an inlet nipple 11 of the discharge manifold block 6 by another short connecting tube also not shown in FIGS. 2-4. Formed by ducts within the manifold block 4 are a milk supply path 12 which communicates with the inlet and outlet nipples 7, 8, a washing fluid supply path 13 which communicates with an inlet nipple 14 for washing fluid and with the outlet nipple 8, an air supply path 15 which communicates with an inlet nipple 16 for pressurised air and with the outlet nipple 8, a return milk path 17 which connects the milk supply path 12 to an outlet nipple 18, and a drain path 19 which connects the milk supply path 12 to an outlet nipple 20 for connection of a tube leading to drain. The washing fluid supply path 13, the air supply path 15, the return milk path 17 and the drain path 19 can be selectively opened and closed by respective solenoid actuated membrane valves 21, 22, 23 and 24, there being two valve actuators mounted on each of the opposite main faces of the manifold block 4. The milk supply path 12 is selectively openable and closeable by a solenoid actuated membrane valve 25, the valve actuator being mounted to an edge face of the manifold block opposite that at which the nipples 14, 16, 18 and 20 are located.

Similar to the induction system manifold block, the manifold block 6 of the discharge system includes ducts forming a common discharge path 26 communicating with the inlet nipple 11, a first milk sample discharge path 27 connecting the common discharge path 26 to a first sample discharge nipple 28, a second milk sample discharge path 29 connecting the common discharge path 26 to a second sample discharge nipple 30, a third milk sample discharge path 31 connecting the common discharge path 26 to a third sample discharge nipple 32, and a fourth milk sample discharge path 33 connecting the common discharge path 26 to a fourth sample discharge nipple 34. The first, second, third and fourth sample discharge paths 27, 29, 31, 33 can be selectively opened and closed by respective solenoid actuated membrane valves 35, 36, 37, 38, there being two valve actuators mounted on each of the opposed main faces of the manifold block 6. A further duct in the manifold block 6 forms a drain path 39 connecting the common discharge path 26 to a nipple 40 to which a tube can be connected leading to drain. The drain path 39 is selectively openable and closable by a solenoid actuated membrane valve 41 mounted to an edge face of the manifold block 6 opposite that at which the sample discharge nipples 28, 30, 32 and 34 are disposed. Each of the valves 21-25, 35-38 and 41 is closed when its solenoid is not energised.

With the pump unit 1 disposed between and connected by short tubes to the induction system 3 and the discharge system 5 a compact assembly is obtained.

A system for supply for washing fluid, which may be water, to the inlet nipple 14 of the washing fluid supply path 13, includes a pressure regulator 44, a pressure indicator 45 and a check valve 46. A system for supply of pressurised air to the inlet nipple 16 of the air supply path 15 includes a first air pressure regulator 47, a first pressure indicator 48, a check valve 49, and connected in parallel with the first pressure regulator a second pressure regulator 50, a second pressure indicator 51 and an air pressure control valve 52 which is solenoid actuated valve. When the valve 52 is closed the air supply system will supply air at a higher pressure, e.g. 3 bar set by the first regulator 47, and when the valve 52 is opened the pressurised air supply system will supply air at a lower pressure, e.g. 1 bar, set by the second pressure regulator 50.

Figure 5:
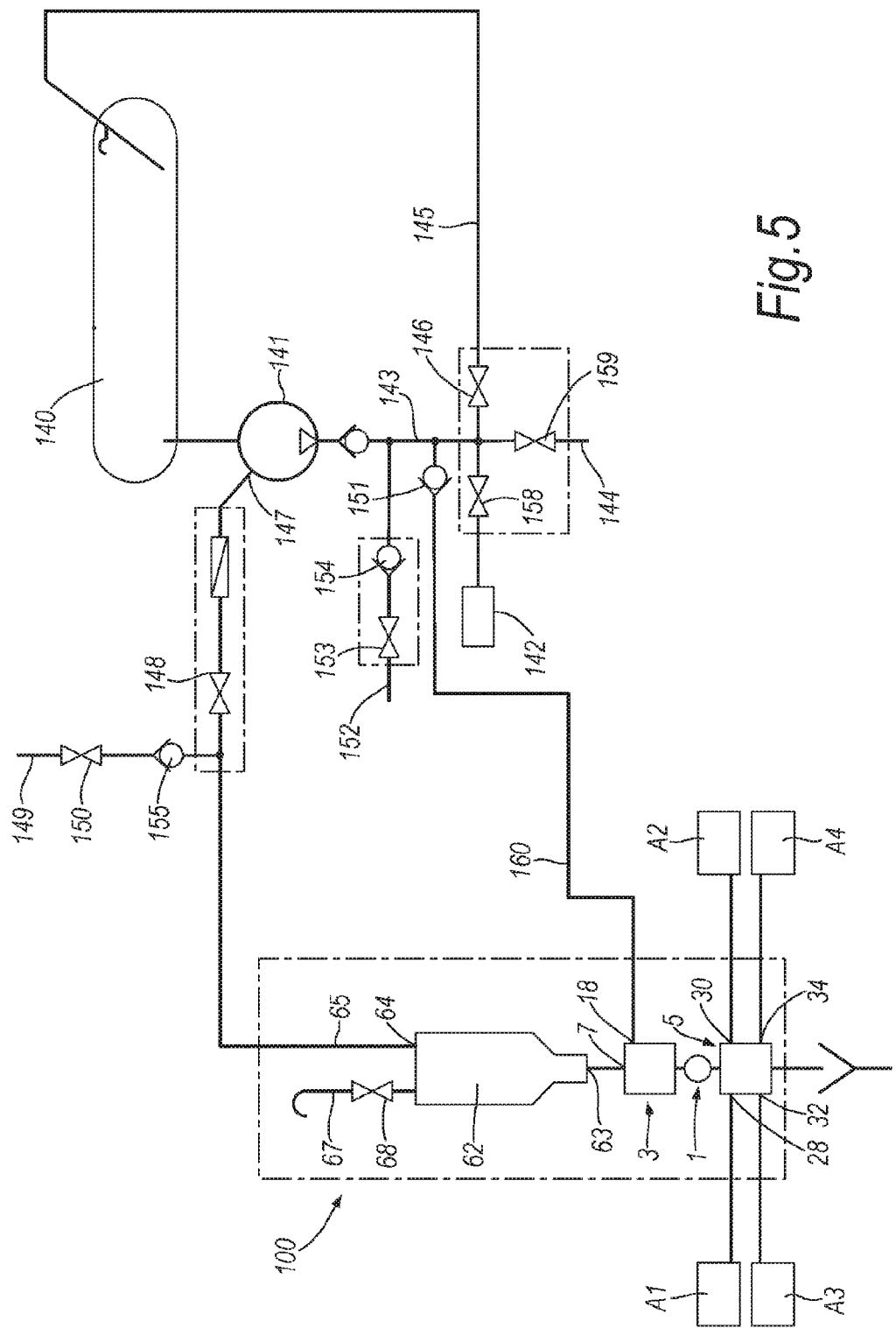
FIG. 5 is a schematic representation showing a milk supply system for delivery of milk to the milk sampling system of FIG. 1 from an automatic milking machine.

The inlet nipple 7 of the induction manifold block 4 is connected by a tube to a bottom outlet 63 of a container or chamber 62 having an inlet 64 connected to a flow line 65 leading from an automatic milking machine, as shown in FIG. 5, for supply of milk into the chamber 62. The chamber 62 also has a vent opening connected by an air flow line 67 to atmosphere. The air flow line 67 can include a valve 68 for closing this flow line. The milk sampling system 100 embodying the invention is connected to collect and sample milk from the vacuum milking system of the automatic milking machine. The milking machine includes a receiver 140 for receiving milk extracted from the udder of an animal during milking. An outlet of the receiver 40 is connected to the inlet of a milk pump 141, the main outlet of which is arranged to be connected to a bulk storage tank 142 via a milk line 143 and valve 158. Branched from the milk line 143 are a drain line 144 equipped with a drain valve 159 and through which milk can be discharged if it is unsuitable for collection in the bulk storage tank, and a mixing line 145 which leads back to the receiver 140 and includes a valve 146 to open and close the mixing line 145. As shown the pump 141 is equipped with a second outlet 147 through which an amount of milk proportional to the total amount of milk passing through the pump is discharged, the pump outlet 147 being connected to the inlet flow line 65 of the milk sampling system through a sampling valve 148. Also connected to the flow line 65 downstream of the valve 48 is an air pressure supply line 149 fitted with a valve 150 and a check valve 155.

The outlet nipple 18 of the milk return path 17 of the sampling apparatus is connected to the pump discharge line 143 by a tube 160 and via a check valve 151. Also connected to the pump discharge line 143 is an air pressure supply line 152 with control valve 153 and check valve 154 for supply of purging air at the end of milking.

During milking of an animal the receiver 140 is subjected to the milking vacuum and receives the milk extracted from the udder of the animal by the teat cups and the vacuum applied thereto. A minor sampling portion of the milk can be directed to the milk sampling apparatus 100, but different methods may be followed in this respect. In a first method the milk mixing line 145 is not used, and the milk is simply pumped from the receiver 140 to the milk tank 142 (unless it is to be discharged to drain) and a proportional amount of milk is discharged through the second pump outlet 147 and through the flow line 165 into the chamber 62 of the sampling apparatus. The sample valve 148 may be opened after a short delay to minimise carry over of milk from the previous milking of another animal. Alternatively, the milk may be collected in the receiver 140 and circulated by the pump 141 and the mixing line 145 by opening valve 146 while valves 158 and 159 remain closed. This circulation of milk ensures good mixing of the milk so that the entire volume of milk is of substantially uniform consistency whereas the consistency generally varies in the course of emptying an udder. When the mixing is completed the valve 146 is closed and the valve 158 is opened so that the milk will be transported by the pump 141 to the bulk milk tank 142. During this phase of emptying the receiver either a substantially fixed quantity of the milk can be transferred through the flow line 65 into the chamber 62 of the sampling apparatus, or a proportional amount of the milk extracted from the udder during milking can be transferred to the chamber 62 of the milk sampling apparatus.

During the supply of milk to the chamber 62 the valves 21-25, 35-38 and 41 of the sampling system remain closed, but the valve 68 is held open to allow air from inside the chamber to escape to atmosphere to avoid a pressure build up in the chamber as it fills with milk. If the amount of milk delivered into the chamber exceeds the maximum volume of the chamber the surplus milk may be allowed to overflow through the flow line 67 connected to atmosphere. When all of the milk to be collected for sampling has been delivered into the sampling chamber 62 the milk collected in the chamber can be agitated and mixed to ensure that the milk samples to be delivered will be representative of the composition of all of the milk collected in the chamber. For this purpose, with the inlet 64 of the chamber connected to the vacuum of the milking system through the flow line 65, and the valve 68 of the line 67 which is connected to atmosphere closed, solenoid valve 24 of the drain path 19 in induction manifold block 4 can be opened so that air is drawn in through the line 24 and bubbles upwardly through the milk in the chamber 62 to mix the milk. After an adequate mixing time the valve 24 is closed again. By closing valve 148 and opening the air valve 155 air under pressure can if desired be delivered into the chamber 62 above the surface level of the milk, to assist subsequent delivery of milk through the outlet 63 of the chamber.

The sample discharge nipples 28, 30, 32, 34 can be connected by tubes to respective milk analysing means A1, A2, A3, A4 such as for measuring different components or parameters of the milk, as described in EP 1381269 B1. At the time of sampling milk from the milking of an individual animal, a discrete milk sample can be discharged to any one or more of the four analysing means A1-A4 as may be desired by appropriate operation of the control device of the milk sampling system. The control device or control unit can be connected to the computer system of the automatic milking machine for receiving commands as to the samples to be discharged.

When the milk has been delivered into the chamber 62 and mixed as described above the discharge of the one or more samples can commence. The valves 25 and 41 are opened and the pump 2 is operated to pump a quantity of milk from the chamber 62 into the sampling apparatus sufficient to pre-fill the sampling system with milk, after which the drain valve 41 is closed to prevent any further milk discharge to drain and the pump is stopped. To discharge a milk sample to a first analysing means A1 through the first sample discharge path 27, the valve 35 is opened and the pump 2 is operated so that a predetermined quantity of milk is delivered through the discharge path 27 to the nipple 28. The valve 25 in the milk supply path is then closed and the pump is stopped. Next the valve 22 in the air supply path is opened and the pump 2 is operated again so that air at the pressure set by the first pressure regulator 47 is admitted and is passed through the pump so that the milk sample is pumped and pushed by the air through the first discharge path 27 to the first analysing means A1. The valves 22 and 35 are closed and the pump is stopped when the milk sample has been pumped/pushed to the analyser.

When a milk sample is to be discharged through the second milk sample discharge path 29 to the second milk analysing means A2 the foregoing procedure is followed but with the valve 36 being opened rather than the valve 35. Similarly when a milk sample is to be discharged through the third milk sample discharge path 31 the same procedure is followed with the valve 37 being opened instead of valve 35, and when a milk sample is to be discharged through the fourth sample discharge path 33 the same procedure is also followed but with the valve 38 opened and the other discharge path valves 35, 36 and 37 held closed. It will be appreciated that by suitable control of the pump 2 and the valves milk samples of desired quantity can be discharged to any one, two, three or all four of the discharge paths to the corresponding analysing means A1-A4. The respective milk samples can be of the same or different predetermined quantities as required.

After the required milk sample or samples have been discharged and delivered to the analysing means as described above, milk remaining in the chamber 62 can be returned to the automatic milking machine to be conveyed to the bulk tank 142. For this purpose the valve 23 in the milk return path 17 is opened. It may be noted that the metering pump 2 is not required to return the excess milk, this instead being achieved as a result of the air under pressure supplied into the chamber 62 from the air pressure supply line 149 and through the flow line 65. Alternatively, if the milk in the chamber 2 is to be dumped, e.g. if it is judged to be of too poor quality to be transported to the bulk milk tank 142, it can be directed to drain by opening the valve 24 in the drain path 19. In addition, milk in the sampling apparatus can also be directed to drain downstream of the pump 2 by opening the valve 41 in the drain path 39 of the discharge manifold block 6.

After one more milk samples have been discharged and delivered to the milk analysing means, the milk sample paths can be flushed clean and dried in preparation for delivery of samples of milk from another animal. For this purpose the valve 21 in the cleaning water supply path 13 is opened, the valve 35 in the first sample discharge path 27 (if a sample was discharged through this path) is opened and the pump 2 is turned on. After adequate flow of washing water through the sample discharge path 27 the valve 35 is closed and the valve 36 in the second sample discharge path is opened (if this path is to be flushed with water). When sufficient water has been directed through the second discharge flow path valve 36 is closed and for flushing the third sample discharge path 31 the valve 37 is opened. When the third discharge path has been suitably flushed with water the valve 37 is closed again and the valve 38 can be opened to flush with cleaning water the fourth sample discharge path 33. After appropriate flow of water through the fourth sample discharge path the valve 38 is closed again. Thus, the flushing water can be supplied for flushing clean, that is to remove any milk sample remnants from each of the sample discharge paths through which samples were discharged during the previous milk sampling. Finally, the valve 41 can be opened so that cleaning water passes through and flushes away any remaining milk in the drain path 39. The valve 21 is then closed to shut off the water supply, the pump 2 is turned off and the drain valve 41 is closed.

For drying the milk paths which have been flushed with cleaning water the same sequence of valve operations can be followed as that applied for flushing the sample discharge paths with water, but with the valve 22 in the air supply path 15 instead of the water valve 21 opened. In this manner the milk sample discharge paths can be dried and any risk of the subsequent milk samples delivered to the analysing means being contaminated or diluted with water used for flushing is avoided. In the drying phase of operation the air pressure control valve 52 is opened so that the air is delivered into the air supply path at the pressure set by the second pressure regulator 50.

After all of the valves have been closed and the metering pump 2 has been turned off at the end of the drying phase, the sampling system is ready for sampling the milk obtained from the next animal milked by the automated milked machine. In fact the filling of the chamber 2 with the milk of the next animal can take place during the water flushing and drying of the sample discharge paths and lines to the analysing means.

While a milk sampling system of currently preferred construction and its operation have been described it will be appreciated that modifications and variations are possible and occur to those skilled in the art without departing from the scope of the invention. By way of example it may be mentioned that more, or indeed less, than four sample discharge paths with associated control valves could provided as desired. Furthermore, if required at least one sample discharge path could be connected to an apparatus for directing the samples into collection tubes for transport to a remote laboratory for analysis.

The invention claimed is:

1. A milk sampling system, comprising:
   a control device;
   a milking machine;
   a milk flow line (65) leading from the milking machine, the flow line providing a path for receiving milk extracted by the milking machine from an individual animal;
   a pump (2) having a pump inlet (9) a pump outlet (10);
   an induction system having plural inlets (7, 14, 16) and plural outlets (8, 18, 20),
   an upstream side of a first of the inlets (14, 16) being connected to a first fluid source and, a downstream side of the first inlet being connected to a first fluid supply path of the induction system,
   an upstream side of a second of the inlets (14, 16) being connected to a second fluid source and, a downstream side of the second inlet being connected to a second fluid supply path of the induction system,
   an upstream side of a third of the inlets (7) being connected to the milk flow line to receive the milk from the milking machine and a downstream side of the first inlet (7) being connected to a milk supply path (12) within the induction system;
   first, second, and third induction system valves (25, 21, 22) that respectively control a flow of fluid within each of the first fluid supply path, the second fluid supply path, and the milk supply path, each of the first, second, and third induction system valves being actuated by the control device,
   a first of the outlets (8) connecting each of the first fluid supply path, the second fluid supply path, and the milk supply path (12) to the pump inlet (9);
   a discharge system having an inlet (11) connected to the pump outlet (10), the inlet (11) connecting the pump outlet (10) to each of a plurality of discharge paths (27, 29, 31, 33), each discharge path having an outlet (28, 30, 32, 34) connected respectively to different milk analyzing devices (A1, A2, A3, A4), to selectively deliver, from the received milk of the individual animal, discrete milk samples for analysis to the milk analyzing devices (A1, A2, A3, A4), each discharge path having flow controlled by a respective discharge system valve (35, 36, 37, 38) to a respective one of the milk analyzing devices (A1, A2, A3, A4) and thereby controls the flow of the milk within that discharge path, each discharge system valve being actuated by the control device, each milk analyzing device performing a type of milk analysis different from types of milk analysis performed the other milk analyzing device(s),
   wherein the control device controls each of the induction system valves and the discharge system valves to successively forward each of discrete samples of the milk received from the individual animal, via the pump (2) and via different respective discharge paths, to respective selected ones of the plural milk analyzing devices for analysis,
   wherein the control device opens a first of the induction system valves (25) and a first of the discharge system valves (35) to define a first discharge path that includes the milk supply path of the induction system and the pump, to forward a first milk sample to a first of the milk analyzing devices (A1) for a first type of milk analysis of the milk from the individual animal, and
   wherein the control device, subsequent to forwarding the first milk sample via the first discharge path, closes the first of the discharge system valves (35), and opens a second of the discharge system valves (36) to define a second discharge path that includes the milk supply path of the induction system and the pump, to forward a second milk sample to a second of the milk analyzing devices (A2) for a second type of milk analysis of the milk from the individual animal, and
   wherein at a time of sampling the milk from the milking of the individual animal, by operation of the control device the discrete milk samples are selectively successively discharged to any of the milk analyzing devices.

2. A milk sampling system according to claim 1, wherein, the first fluid source is a pressurized gas source, and
   the control device, to forward the milk sample to the first milk analyzing device (A1), further opens a second of the induction system valves (22) to admit pressurized gas from the pressurized gas source to push the first milk sample, via the pump, through the first discharge path to the first milk analyzing device (A1).

3. A milk sampling system according to claim 2, wherein, the second fluid source is a washing fluid source,
   the discharge system further includes i) a common discharge path (26) connecting the inlet of the discharge system, via the pump, to each of the plurality of discharge paths (27, 28, 31, 33) connected to the plurality of milk analyzing devices (A1, A2, A3, A4), ii) a drain path (39) connected to the common discharge path (26) for discharging residual milk from the discharge system, and iii) a discharge path valve (41) controlled by said control device,
   to discharge the residual milk from the discharge system, the control device opens a third of the induction system valves (21) and the discharge path valve (41) of the discharge system valves (35) to forward a washing fluid from washing fluid source via the induction system for flushing away the residual milk in the drain path (39), and
   to dry that the drain path (39), the control device opens the second induction system valve (22) and the discharge path valve (41) of the discharge system valves (35) to forward pressurized gas from the pressurized gas source via the induction system for drying the drain path (39).

4. A milk sampling system according to claim 2, wherein, wherein the pressurized gas is air,
   the pump is a metering pump calibrated to deliver a fixed quantity for each stroke of the pump, and
   at least one of the induction system valves and the discharge system valves is a solenoid valve.

5. A milk sampling system according to claim 1, wherein, the induction system comprises a first manifold block carrying the induction system valves (21, 22, 25),
   the plural inlets (7, 14, 16) and the plural outlets (8, 18, 20) of the induction system are each at an outer face of the first manifold block,
   the discharge system comprises a second manifold block carrying discharge system valves (35, 36, 37, 38, 41),
   the inlet and the outlets of the discharge system are each at an outer face of the second manifold, and
   the first and second manifold blocks are separate discrete blocks.

6. A milk sampling system according to claim 5, wherein, the first and second manifold blocks are mounted together with the pump positioned therebetween.

7. A milk sampling system according to claim 1, wherein, the induction system further includes
i) a drain path (18) and a drain path device (23) for selectively opening and closing communication between the drain path and the milk supply path, and
ii) a milk return path (19) and a milk return device (24) for selectively opening and closing communication between the milk return path and the milk supply path.

8. A milk sampling system according to claim 1, wherein, the induction system includes a pressure control device in a supply path of pressurized gas, and
the gas pressure control device is operable for the pressurized gas to be supplied at different pressures.

9. A milk sampling system according to claim 1, wherein the control device controls the induction system and the discharge system so that after delivery of a milk sample through at least one discharge path, washing fluid is supplied through a washing fluid supply path and is conveyed through the pump and through the at least one discharge path, and air for drying is supplied through a pressurized gas supply path and is conducted through the pump and through the at least one discharge path.

10. A milk sampling method, comprising:
operating a milking machine to extract milk from an individual animal, and having the extracted milk flow through a milk flow line (65) leading from the milking machine, the milk flow line thereby providing a path for receiving the milk from the milking machine and extracted from an individual animal;
operating a control device connected to i) an induction system (4) with plural fluid supply paths (12, 13, 15), each supply path being connected to a respective one of plural fluid sources, each supply path including a respective induction system valve (21, 22, 25) that controls a flow of fluid within that supply path, each induction system valve being actuatable by the control device, one of the fluid sources being a milk source (7) connected to the flow line that provides the path for receiving the milk extracted from the individual animal, the induction system having an outlet (8), ii) a discharge system having a plurality of discharge paths (27, 29, 31, 33) connected respectively to different milk analyzing devices (A1, A2, A3, A4), to selectively deliver discrete milk samples for analysis to the milk analyzing devices (A1, A2, A3, A4), each discharge path including a respective discharge system valve (35, 36, 37, 38) that discharges to a respective one of the milk analyzing devices (A1, A2, A3, A4) and controls the flow of the fluid within that discharge path, each discharge system valve being actuatable by the control device, each milk analyzing device performing a type of milk analysis different from types of milk analysis performed the other milk analyzing device(s), the discharge system having an inlet (11) and iii) a pump (2) having a pump inlet (9) connected to the outlet of the induction system and a pump outlet (10) connected to the inlet of the discharge system so that the pump forwards fluid from the induction system into the discharge system,
wherein said operating the control device controls each of the induction system valves and the discharge system valves to successively forward discrete samples of the milk, via the pump and via different respective discharge paths, to respective selected ones of the plural milk analyzing devices for analysis,
wherein the control device opens a first of the induction system valves (25) and a first of the discharge system valves (35) to define a first discharge path via the pump to a first of the milk analyzing devices (A1), and forwards a first milk sample to the first of the milk analyzing devices (A1) for a first type of milk analysis of the milk from the individual animal,
wherein, after forwarding the first milk sample to the first of the milk analyzing devices (A1), the control device closes the first of the discharge system valves (35), and opens a second of the discharge system valves (36) to define a second discharge path via the pump to a second of the milk analyzing devices (A2), and forwards a second milk sample to the second of the milk analyzing devices (A2) for a second type of milk analysis of the milk from the individual animal, and
wherein at a time of sampling the milk from the milking of the individual animal, by operation of the control device the discrete milk samples are selectively successively discharged to any of the milk analyzing devices.

11. A milk sampling method according to claim 10, wherein,
the fluid sources connected to the induction system include a pressurized gas source,
the method further comprises selectively opening and closing communication between the drain path and the milk supply path, and
the method further comprises the control device, to forward the milk sample to the first milk analyzing device (A1), further opens another of the induction system valves (22) to admit pressurized gas from the pressurized gas source to push the first milk sample through the first discharge path to the first milk analyzing device (A1).

12. A milk sampling method according to claim 10, wherein,
the fluid sources connected to the induction system further include a washing fluid source,
the discharge system further includes i) a common discharge path (26) connecting the inlet of the discharge system to each of the plurality of discharge paths (27, 29, 31, 33) connected to the plurality of milk analyzing devices (A1, A2, A3, A4), ii) a drain path (39) connected to the common discharge path for discharging residual milk from the discharge system, and iii) a discharge path valve (41) controlled by said control device, and
to discharge the residual milk from the discharge system, the control device opens a third of the induction system valves (21) and the discharge path valve (41) of the discharge system valves (35) to forward a washing fluid from washing fluid source via the induction system for flushing away the residual milk in the drain path (39), and
subsequent to flushing away the residual milk, to dry that the drain path (39), the control device opens the other induction system valve (22) and the discharge path valve (41) of the discharge system valves (35) to forward pressurized gas from the pressurized gas source via the induction system for drying the drain path (39).

13. A milk sampling method according to claim 12, wherein,
the first and second manifold blocks are mounted together with the pump positioned therebetween.

14. A milk sampling method according to claim 10, wherein,
the fluid sources connected to the induction system include a washing fluid source and a pressurized gas source,
the discharge system further includes i) a common discharge path (26) connecting the inlet of the discharge system, via the pump, to each of the plurality of discharge paths (27, 28, 31, 33) connected to the plurality of milk analyzing devices (A1, A2, A3, A4), ii) a drain path (39) connected to the common discharge path for discharging residual milk from the discharge system, and iii) a discharge path valve (41) controlled by said control device, and
to discharge the residual milk from the discharge system, the control device opens a third of the induction system valves (21) and the discharge path valve (41) of the discharge system valves (35) to forward a washing fluid from washing fluid source via the induction system for flushing away the residual milk in the drain path (39), and
subsequent to flushing away the residual milk, to dry that the drain path (39), the control device opens a fourth of the induction system valves (22) and the discharge path valve (41) of the discharge system valves (35) to forward pressurized gas from the pressurized gas source via the induction system for drying the drain path (39).

15. A milk sampling method according to claim 10, wherein,
wherein the pressurized gas is air,
the pump is a metering pump calibrated to deliver a fixed quantity for each stroke of the pump, and
at least one of the induction system valves and the discharge system valves is a solenoid valve.

16. A milk sampling method according to claim 10, wherein,
the induction system comprises a first manifold block carrying the induction system valves (21, 22, 25), and
the discharge system comprises a second manifold block carrying discharge system valves (35, 36, 37, 38, 41), the first and second manifold blocks being separate discrete blocks.

17. A milk sampling method according to claim 10, wherein,
the induction system further includes i) a drain path (18) and a drain path device (23), and ii) a milk return path (19) and a milk return device (24),
the method further comprises selectively opening and closing communication between the drain path and the milk supply path, and
the method further comprises selectively opening and closing communication between the milk return path and the milk supply path.

18. A milk sampling method according to claim 10, wherein,
the induction system includes a pressure control device in a supply path of pressurized gas, and
the method further comprises operating the gas pressure control device for the pressurized gas to be supplied at different pressures.

19. A milk sampling method according to claim 10, wherein,
the method further comprises the control device controlling the induction system and the discharge system so that after delivery of a milk sample through at least one discharge path, washing fluid is supplied through a washing fluid supply path and is conveyed through the pump and through the at least one discharge path, and air for drying is supplied through a pressurized gas supply path and is conducted through the pump and through the at least one discharge path.

20. A milk sampling system, comprising:
a milking machine;
a milk flow line (65) leading from the milking machine, the milk flow line providing a milk supply path for receiving milk extracted by the milking machine from an individual animal;
a fluid conveying device operatively connected to the milk supply path to receive the milk of the individual animal from the milking machine, the fluid conveying device including
i) an induction system comprising plural supply paths (12, 13, 15) with respective inlets (7, 14, 16) connected to a plurality of fluid sources including a milk supply inlet (7) connected to the milk supply path for receiving the milk extracted by the milking machine from the individual animal, the plural supply paths having a common outlet (8), and
ii) a discharge system comprising plural discharge paths, each discharge path having an outlet (28, 30, 32, 34) connected respectively to one of different milk analyzing devices (A1, A2, A3, A4), the plural discharge paths having a common inlet (11);
a pump (2) connecting to the common outlet (8) of the induction system to the common inlet (11) of the discharge system, the pump conveying fluids and the milk received by the supply paths of the induction system from the common outlet (8) of the induction system to the common inlet (11) of the discharge system; and
a control device operatively connected to the fluid conveying device and to the pump,
wherein the control device controls the induction system to selectively connect the pump to the plurality of fluid sources including to the milk supply path,
wherein the control device further controls the fluid conveying device and the pump to forward discrete samples of the milk i) received from the milk supply path at the milk supply inlet (7), moved through the milk supply path to the common outlet (8) of the induction system, and conveyed via the pump (2) to the common inlet (11) of the discharge system, ii) to respective different ones of the discharge paths for analysis by respective different ones of the milk analyzing devices, to thereby successively deliver the discrete milk samples via the respective discharge paths for analysis by the respective different milk analyzing devices, and
wherein at a time of sampling the milk from the milking of the individual animal, by operation of the control device the discrete milk samples are selectively successively discharged to any of the milk analyzing devices.

* * * * *